United States Patent [19]
Aspel

[11] Patent Number: 5,836,767
[45] Date of Patent: Nov. 17, 1998

[54] DENTAL SHIM

[76] Inventor: Thomas E. Aspel, 3149 Old Post Rd., Fallbrook, Calif. 92028

[21] Appl. No.: 893,183

[22] Filed: Jul. 15, 1997

[51] Int. Cl.$^6$ .................................................. A61C 3/00
[52] U.S. Cl. ............................................ 433/141; 433/229
[58] Field of Search .............................. 433/3, 4, 72, 141, 433/147, 229

[56] References Cited

U.S. PATENT DOCUMENTS

| | | | |
|---|---|---|---|
| 1,108,493 | 8/1914 | Federspiel | 433/4 X |
| 3,080,654 | 3/1963 | White | 433/140 X |
| 3,727,316 | 4/1973 | Goldberg | 433/4 |
| 3,755,902 | 9/1973 | Northcutt | 156/584 |
| 3,911,583 | 10/1975 | Hoffman | 29/268 |
| 3,986,265 | 10/1976 | Cusato | 156/584 |
| 4,708,651 | 11/1987 | Buchanan | 433/72 X |
| 4,997,368 | 3/1991 | Mayer et al. | 433/72 |
| 5,039,302 | 8/1991 | Keys | 433/3 |
| 5,395,236 | 3/1995 | Khouri | 433/4 |
| 5,538,421 | 7/1996 | Aspel | 433/4 |

*Primary Examiner*—Nicholas D. Lucchesi
*Attorney, Agent, or Firm*—Frank J. McGue

[57] ABSTRACT

A dental shim is disclosed for insertion between a tooth and one jaw of a dental pliers. The dental shim comprises a handle and an elongated shim portion extending outward from the handle. The elongated shim portion has a base, a side and a hypotenuse. The base and the hypotenuse are joined along one edge at a plurality of angles. The base engages a tooth and the hypotenuse engages one jaw of a dental pliers.

17 Claims, 1 Drawing Sheet

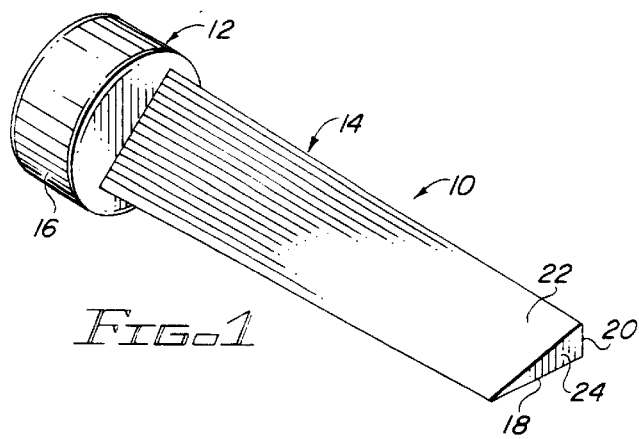
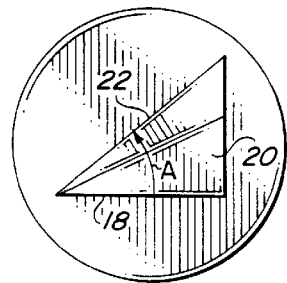
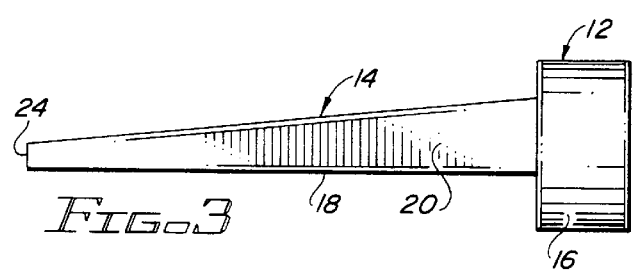
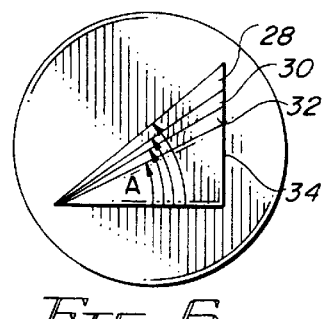
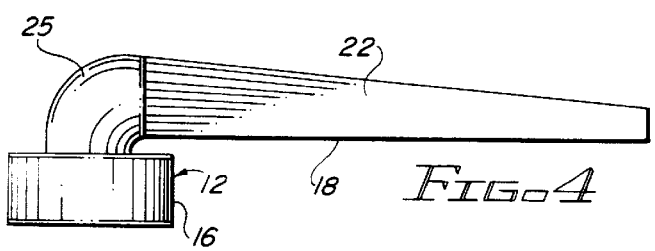
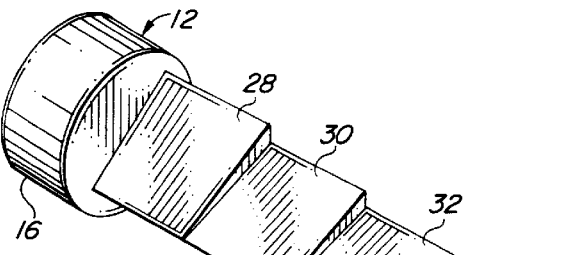
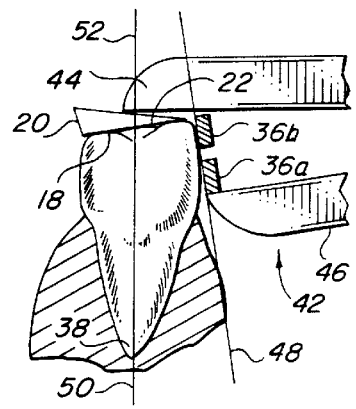
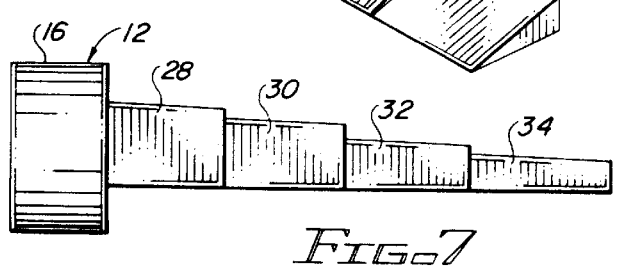
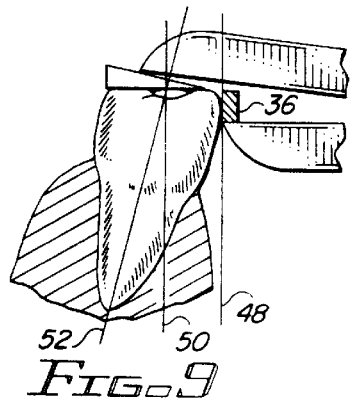

DENTAL SHIM

TECHNICAL FIELD

This invention relates to the field of dental appliances, and, more particularly, to dental appliances used to remove orthodontic braces, bands, brackets, glue, cementing media and the like from tooth surfaces.

BACKGROUND OF THE INVENTION

In dentistry, and specifically in the branch of dentistry called orthodontics, often brackets, bands, buttons, cleats and braces (collectively "attachments") are placed on the teeth of a patient to correct irregularities. Various cements are used to bond the attachments to the tooth enamel. However, at the end of the prescribed course of treatment, removal of such attachments and the associated cement is a difficult problem.

Current devices for removal of such attachments generally comprise pliers having one jaw longer than the other. The longer jaw is designed to provide a fulcrum by resting upon the occlusal (biting) surfaces of a tooth while the shorter jaw scrapes the buccal or facial surfaces of the tooth to chip away cement and engage the orthodontic devices for removal.

However, in most presently known designs, when the cutting edge of the shorter jaw is positioned to remove cement or attachments, the force created thereby is not directed longitudinally down the axis of the tooth. Instead, such force includes a component which tips or luxates the tooth buccally or facially. Such tipping or luxation results in pain caused by compression of the periodontal ligament and bone around the tooth.

Various solutions have been devised in attempts to overcome the problem. U.S. Pat. No. 3,986,265 entitled "Orthodontic Tool for Removing Epoxy Secured Brackets and Epoxy Residue" which issued on Oct. 19, 1976 to Cusato discloses an orthodontic tool comprising a pliers type device having a plastic cap which engages the upper or outer edge of tooth.

U.S. Pat. No. 3,755,902 entitled "Tool For Removing A:n Orthodontic Onlay that has been Cemented to the Front Surface of a Tooth" which issued on Sep. 4, 1973 to Northcutt shows orthodontic pliers having a cap mounted on an elongated jaw.

U.S. Pat. No. 3,911,583 entitled "Pliers-Type Band and Cement Remover which issued on Oct. 14, 1975 to Hoffman and U.S. Pat. No. 5,538,421 entitled "Dental Instrument" which issued on Jul. 23, 1996 to Aspel (the present applicant) show prior efforts to minimize discomfort to a patient having orthodontic devices removed.

None of the known prior art disclose the dental shim set forth herein.

SUMMARY OF THE INVENTION

It is an object of this invention to provide a dental shim which allows a user to direct the force vector along the longitudinal axis of a tooth.

It is a further object of this invention to provide a dental shim which can be used with the current plier devices to direct the force vector along the longitudinal axis of a tooth.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWINGS

The present invention may be more readily described by reference to the accompanying drawings in which:

FIG. 1 is a perspective view of one embodiment of the present invention;

FIG. 2 is a front view of the embodiment of FIG. 1;

FIG. 3 is a left side view of the embodiment of FIG. 1;

FIG. 4 is a top side view of an alternate embodiment of FIG. 1;

FIG. 5 is a perspective view of another embodiment of the present invention;

FIG. 6 is a front view of the embodiment of FIG. 5;

FIG. 7 is a left side view of the embodiment of FIG. 5;

FIG. 8 is a side view of the present invention in use on bicuspid tooth; and

FIG. 9 is a side view of the present invention in use on an bicuspid tooth.

DESCRIPTION OF THE PREFERRED EMBODIMENT

Referring more particularly to the drawings by characters of reference, FIGS. 1–4 disclose one embodiment of a dental shim 10. Dental shim 10 comprises a handle 12 and a elongated shim portion 14 extending longitudinally outward from handle 12. As illustrated, handle 12 is a squat cylindrical shape having 16 suitable for a dentist to grasp in one hand. Sidewall 16 allow the dentist to easily rotate dental shim 10 along its longitudinal axis.

As best seen in FIG. 2, elongated shim portion 14 extends longitudinally outward from handle 12. In profile, elongated shim portion 14 is a sloping wedge shape which presents a right triangular cross section having a base 18, a side 20 and a hypotenuse 22. In the embodiment of FIG. 1, base 18 is a rectangular planar surface having a constant width of, preferably, between about 1 centimeter to 3 centimeters, most preferably, about 1.25 centimeters.

Hypotenuse 22 is joined along one edge to a corresponding edge of base 18 at an acute angle A while side 20 extends between the edges of base 18 and hypotenuse 22 opposite angle A. Side 20 and hypotenuse 22 are also planar rectangular surfaces whose widths vary as the angle A varies in accordance with the appropriate well known trigonometric functions. Preferably, in each dental shim 10 angle A is about 40° at handle 12 to 5° at an end 24 opposite handle 12, but most preferably from between 30° to 35° from handle 12 to 15° at end 24.

In the preferred embodiment, elongated shim portion 14 is from 3 centimeters to 15 centimeters long, most preferably about 5 centimeters to eight centimeters in length.

In an alternate embodiment seen in FIG. 4, handle 12 and elongated shim portion 14 are joined by an elbow 25 which bends 90° from elongated shim portion 14. Placement of handle 12 off center from elongated shim portion 14 may be more comfortable for some dentists in use. Those skilled in the art will recognize that elbow 25 need not be limited to 90° and that other angles may be employed if desired.

In an alternate embodiment shown in FIGS. 5–7, the sloping wedge shaped shim portion 14 is replaced with a stepped wedged shaped shim portion 26. In this embodiment, stepped wedge portion 26 comprises a plurality of sections 28, 30, 32 and 34 having different angles A as best seen in FIG. 6. However, within each section 28, 30, 32 and 34, angle A remains constant. One embodiment has angle A being 40, 35, 30 and 25 degrees for sections 28, 30, 32 and 34, respectively. In another embodiment, angle A is 35, 30, 20 and 10 degrees for sections 28, 30, 32 and 34, respectively. The width of base 18 and the overall length of stepped wedge portion 26 are as previously described.

Dental shim 10 can be manufactured from a variety of materials, but most preferably, plastics. If reusability is desired, dental shim 10 can be made from a harder plastic to resist autoclave temperatures and humidity. On the other hand, a softer plastic material allows a tooth to bite into dental shim 10 to provide a better grip. In addition, it is often preferable to simply discard dental shim 10 after use for sanitary reasons.

As best seen in FIGS. 8 and 9, to remove dental attachments 36 and related cement materials from a bicuspid tooth 38, or any other tooth, a dentist or orthodontist employs a pliers type tool 42 having a long jaw 44 and a short jaw 46. Long jaw 44 would normally engage the top of teeth 38 while short jaw 46 engages attachment 36.

However, the direction of force exerted by short jaw 46 is directed parallel to the tooth face as shown by a line 48 while the force exerted by long jaw 44 is offset from line 48 as shown by a line 50. The angular difference in the direction of forces between lines 48 and 50 creates a torque on the tooth which tips or luxates the tooth thus causing pain or discomfort to the patient. As illustrated by comparing FIGS. 8 and 9, it is understood by those skilled in the art that the direction of force vector 48 changes as short jaw 46 moves up and down the tooth face to engage dental attachments 36 and cement materials at different positions on tooth 38.

To negate the difference in the direction of forces, dental shim 10 is inserted between long jaw 44 and tooth 38. In the illustrations of FIGS. 8 and 9, base 18 is place on top of the tooth while hypotenuse 22 engages long jaw 44. However, those skilled in the art will recognize that shim 10 can be positioned with hypotenuse 22 on the biting surface of the tooth in order to direct the force along the long axis of the tooth opposite the force exerted in certain types of bracket removals.

The dentist, using handle 12, slides dental shim 10 longitudinally to adjust the angle A and laterally to adjust the thickness of dental shim 10 until the the force exerted on tooth 38 is directed along a line 52 which is parallel to line 48 which the dentist determines using both visual and tactile senses. Since the forces are equal and opposite, torque is not exerted on the tooth and thus, no tipping or luxation will occur to cause pain or discomfort.

The major advantage of the present invention over prior methods is the ability to allow the dentist to easily adjust the dental shim 10 while working in the mouth. By moving dental shim 10 laterally, angle A is maintained and the thickness changes.

Although only certain embodiments have been illustrated and described, it will be apparent to those skilled in the art that various changes and modifications may be made therein without departing from the spirit of the invention or from the scope of the appended claims.

What is claimed is:

1. A dental shim for insertion between a tooth and one jaw of a dental pliers, the dental shim comprising:

a handle; and an elongated shim portion extending outward from the handle, the elongated shim portion having a base, a side and a hypotenuse, the base and the hypotenuse joined at a plurality of angles, the base adapted to engage a biting surface of a tooth and the hypotenuse adapted to engage one jaw of a dental pliers.

2. The dental shim of claim 1 wherein the handle is cylindrically shaped having a sidewall suitable for grasping.

3. The dental shim of claim 1 wherein the elongated shim portion is a sloping wedge shape having a right triangular cross section.

4. The dental shim of claim 3 wherein the base is a constant width and the width of the side and the hypotenuse vary in accordance with trigonometric functions based upon the plurality of angles.

5. The dental shim of claim 4 wherein the base is between one and three centimeters wide.

6. The dental shim of claim 3 wherein the plurality of angles is a continuity of between 5 degrees and 40 degrees.

7. The dental shim of claim 6 wherein the plurality of angles is a continuity of between 15 degrees and 35 degrees.

8. The dental shim of claim 1 wherein the elongated shim portion is a stepped wedge shape.

9. The dental shim of claim 8 wherein the base is a constant width and the width of the side and the hypotenuse vary in accordance with trigonometric functions based upon the plurality of angles.

10. The dental shim of claim 9 wherein the base is between one and three centimeters wide.

11. The dental shim of claim 8 wherein the plurality of angles are four angles of 10 degrees, 20 degrees, 30 degrees and 35 degrees.

12. The dental shim of claim 11 wherein the plurality of angles are four steps between 25 degrees and 35 degrees.

13. The dental shim of claim 1 wherein the elongated shim portion is from 3 centimeters to 15 centimeters in length.

14. The dental shim of claim 13 wherein the elongated shim portion is five centimeters to eight centimeters in length.

15. The dental shim of claim 1 wherein the handle and the elongated shim portion are joined by an elbow.

16. The dental shim of claim 15 wherein the elbow bends 90° from the elongated shim portion.

17. A dental shim for insertion between a tooth and one jaw of a dental pliers, the dental shim comprising:

a cylindrically shaped handle suitable for grasping; and an elongated shim portion extending outward from the handle, the elongated shim portion having a right triangular cross section, the elongated shim portion having a base, a side and a hypotenuse, the base adapted to engage a biting surface of a tooth and the hypotenuse adapted to engage one jaw of a dental pliers, the base and the hypotenuse joined at a plurality of angles between 5 degrees and 40 degrees, the base having a constant width of between one and three centimeters and the width of the side and the hypotenuse varying in accordance with trigonometric functions based upon the plurality of angles.

* * * * *